United States Patent
Antoku et al.

(10) Patent No.: US 6,867,234 B2
(45) Date of Patent: Mar. 15, 2005

(54) FAT COMPOSITION FOR ORAL OR ENTERNAL ADMINISTRATION AND HEXACOSANOIC ACID DEPRESSANT

(75) Inventors: Yasunobu Antoku, Kurume (JP); Kosuke Tsukamoto, Kurume (JP); Fumihiko Koike, Saga (JP); Takashi Tokuyama, Fukuoka (JP); Hirotoshi Hayasawa, Funabashi (JP); Mitsunori Takase, Saitama (JP); Kyoichi Oshida, Yamato (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 10/415,412

(22) PCT Filed: Nov. 15, 2001

(86) PCT No.: PCT/JP01/09976

§ 371 (c)(1),
(2), (4) Date: Apr. 29, 2003

(87) PCT Pub. No.: WO02/40014

PCT Pub. Date: May 23, 2002

(65) Prior Publication Data

US 2004/0028691 A1 Feb. 12, 2004

(30) Foreign Application Priority Data

Nov. 16, 2000 (JP) ........................... 2000-349818

(51) Int. Cl.$^7$ ..................... A61K 31/20; A61K 31/59; A61K 31/23; A61K 31/07
(52) U.S. Cl. ................... 514/560; 514/167; 514/168; 514/552; 514/725
(58) Field of Search ................... 424/523, 725; 514/167, 552, 560, 725, 168

(56) References Cited

U.S. PATENT DOCUMENTS

| 4,636,494 | A | | 1/1987 | Growdon et al. |
| 5,223,285 | A | | 6/1993 | DeMichele et al. |
| 5,260,067 | A | | 11/1993 | Zheng |
| 5,306,516 | A | | 4/1994 | Letton et al. |
| 5,308,640 | A | | 5/1994 | Baer et al. |
| 5,308,832 | A | * | 5/1994 | Garleb et al. .................. 514/2 |
| 5,370,892 | A | | 12/1994 | El-Nokaly et al. |
| 5,700,782 | A | * | 12/1997 | Cope et al. .................... 514/21 |
| 6,077,828 | A | * | 6/2000 | Abbruzzese et al. ........... 514/21 |
| 6,258,846 | B1 | * | 7/2001 | Hermelin et al. ............ 514/558 |

FOREIGN PATENT DOCUMENTS

| EP | 1 066 816 A1 | 1/2001 |
| FR | 2 761 887 | 10/1998 |
| JP | 6-118078 | 4/1994 |
| JP | 6-169735 | 6/1994 |
| JP | 6-192082 | 7/1994 |
| JP | 9-30962 | 2/1997 |
| JP | 9-30963 | 2/1997 |
| JP | 2884213 | 2/1999 |
| WO | WO 95/06414 | 3/1995 |

OTHER PUBLICATIONS

U.S. Translation of JP 9–30962–A (1997).*
U.S. Translation of JP 9–30963–A (1997).*
The Nutrition Desk Reference, published by Keats Pulishing, inc. (CT), 1985, pp 36–40.*

* cited by examiner

Primary Examiner—Raymond J. Henley, III
(74) Attorney, Agent, or Firm—Nixon & Vanderhye P.C.

(57) ABSTRACT

A fat composition for oral or enteral administration which contains eicosapentaenoic acid and/or a derivative thereof, docosahexaenoic acid and/or a derivative thereof, and a $C_{20}$ or higher monoenoic acid and/or a derivative thereof and functions to diminish hexacosanoic acid; and a hexacosanoic acid depressant which comprises as active ingredients eicosapentaenoic acid and/or a derivative thereof, docosahexaenoic acid and/or a derivative thereof, and a $C_{20}$ or higher monoenoic acid and/or a derivative thereof. They can be prepared by extraction from a fish oil or the like, purification, blending, etc. Based on the function of diminishing hexacosanoic acid, the composition and the depressant produce an aging-inhibitory effect on cell membranes, which is effective in the prevention and treatment of lifestyle-related diseases.

5 Claims, No Drawings

FAT COMPOSITION FOR ORAL OR ENTERNAL ADMINISTRATION AND HEXACOSANOIC ACID DEPRESSANT

This application is the US national phase of international application PCT/JP01/09976 filed Nov. 15, 2001 which designated the U.S.

TECHNICAL FIELD

The present invention relates to a fat composition, which possess hexacosanoic acid depressant function, for oral or enteral administration, and to a hexacosanoic acid depressant with an object of producing an aging-inhibitory effect on cell membranes. In particular, the present invention relates to a fat composition for oral or enteral administration which contains eicosapentaenoic acid and/or a derivative thereof, docosahexaenoic acid and/or a derivative thereof, and a $C_{20}$ or higher monoenoic acid and/or a derivative thereof and functions to diminish hexacosanoic acid; and to a hexacosanoic acid depressant which includes as active ingredients eicosapentaenoic acid and/or a derivative thereof, docosahexaenoic acid and/or a derivative thereof, and a $C_{20}$ or higher monoenoic acid and/or a derivative thereof.

In this specification, the term "Vitamin D" includes Vitamin $D_2$ and Vitamin $D_3$. Accordingly, the term "content of Vitamin D" means the total content of Vitamin $D_2$ and Vitamin $D_3$.

BACKGROUND ART

Some of the inventors of the present invention found that higher monoenoic acids, such as erucic acid and gondoic acid, which are monoenoic acids of $C_{20}$ or higher, possess hexacosanoic acid depressant function and produce an aging-inhibitory effect on cell membranes based on the depressant function, and filed a patent application (which matured as Japanese Patent No. 2,884,213, hereinafter referred to as a prior art 1).

However, problems which should be solved are contained in the prior art as described below.

That is, as disclosed in the above prior art 1, an improver for aging-inhibitory effect on a cell membrane was developed based on hexacosanoic acid depressant effect of active ingredients of higher monoenoic acid and/or a derivative thereof. However, in the prior art 1, the hexacosanoic acid depressant effect was not sufficient when the improver was taken orally or enterally as is partially explained in Examples shown below.

The inventors of the present invention, taking into consideration the above prior art, have performed diligent research to further improve the hexacosanoic acid depressant effect when administered orally or eternally, and have found that some combinations of three kinds of fatty acids including $C_{20}$ or higher monoenoic acid and/or a derivative thereof, eicosapentaenoic acid and/or a derivative thereof, and docosahexaenoic acid and/or a derivative thereof can solve the above-mentioned problems as partially described in Examples shown below.

Accordingly, the purpose of the present invention includes to provide a fat composition for oral or enteral administration having aging-inhibitory effects on a cell membrane, which is effective in the prevention and treatment of lifestyle-related diseases, based on hexacosanoic acid depressant function, and to provided a hexacosanoic acid depressant.

DISCLOSURE OF THE INVENTION

The first aspect of the present invention which solves the above-mentioned problems is a fat composition for oral or enteral administration, which contains eicosapentaenoic acid and/or a derivative thereof, docosahexaenoic acid and/or a derivative thereof, and a $C_{20}$ or higher monoenoic acid and/or a derivative thereof, and which possesses hexacosanoic acid depressant function.

Also, it is preferable that the first aspect of the present invention be a fat composition for oral or enteral administration, which contains eicosapentaenoic acid and/or a derivative thereof, docosahexaenoic acid and/or a derivative thereof, and a $C_{20}$ or higher monoenoic acid and/or a derivative thereof, and which possesses hexacosanoic acid depressant function, in which the content of Vitamin A and Vitamin D per 1 gram of the fat composition is 75 μg or less and 2.5 μg or less, respectively.

The second aspect of the present invention which solves the above-mentioned problems is a hexacosanoic acid depressant which includes as active agents eicosapentaenoic acid and/or a derivative thereof, docosahexaenoic acid and/or a derivative thereof, and a $C_{20}$ or higher monoenoic acid and/or a derivative thereof.

Also, it is preferable that the second aspect of the present invention be a hexacosanoic acid depressant which includes as active agents eicosapentaenoic acid and/or a derivative thereof, docosahexaenoic acid and/or a derivative thereof, and a $C_{20}$ or higher monoenoic acid and/or a derivative thereof, in which the content of Vitamin A and Vitamin D per 1 gram of the hexacosanoic acid depressant is 75 μg or less and 2.5 μg or less, respectively.

BEST MODE FOR CARRYING OUT THE INVENTION

In the following, the present invention will be explained in detail.

Eicosapentaenoic acid and/or a derivative thereof, which is one of the constituents of the fat composition for oral or enteral administration according to the first embodiment of the present invention, is not particularly limited as long as it is pharmaceutically or sitologically permissible. That is, it is possible to use, directly or in suitable combination, natural fat having a large eicosapentaenoic acid content, such as various kinds of fish oil. Also, it is possible to extract and purify eicosapentaenoic acid from natural fat using ordinary methods, such as fractional distillation, crystallization, solvent extraction, urine clathration, and chromatography. More simply, it is possible to use a commercially available eicosapentaenoic acid (a product of Sigma Co.).

Eicosapentaenoic acid derivatives which may be used in the present invention include derivatives of various esters and so forth besides salts of eicosapentaenoic acid. More specifically, examples of the eicosapentaenoic acid derivatives include salts of alkali metals, such as sodium and potassium, esters of lower aliphatic alcohols, such as ethanol, and mono-, di-, and tri-glycerides.

Docosahexanoic acid and/or a derivative thereof, which is one of the constituents of the fat composition for oral or enteral administration according to the first embodiment of the present invention, is not particularly limited as long as it is pharmaceutically or sitologically permissible. That is, it is possible to use, directly or in suitable combination, natural fat having a large docosahexanoic acid content, such as various kinds of fish oil. Also, it is possible to extract and purify docosahexanoic acid from natural fat using ordinary methods, such as fractional distillation, crystallization, solvent extraction, urine clathration, and chromatography. More simply, it is possible to use a commercially available docosahexanoic acid (a product of Sigma Co.).

Docosahexanoic acid derivatives which may be used in the present invention include derivatives of various esters and so forth besides salts of docosahexanoic acid. More specifically, examples of the docosahexanoic acid derivatives include salts of alkali metals, such as sodium and potassium, esters of lower aliphatic alcohols, such as ethanol, and mono-, di-, and tri-glycerides.

$C_{20}$ or higher monoenoic acid and/or a derivative thereof, which is one of the constituents of the fat composition for oral or enteral administration according to the first embodiment of the present invention, may be more specifically one or combination of $C_{20}$ gondoic acid (gondou acid), gadoleic acid, icosenic acid (eicosenic acid), such as 5-icosenic acid, and/or derivative thereof, $C_{22}$ erucic acid, cetolenoic acid, docosenoic acid, such as 5-docosenoic acid, and/or derivative thereof, and $C_{24}$ tetracosenoic acid, such as nervonic acid (ceracorenoic acid, shark oil acid), and/or derivatives thereof.

$C_{20}$ or higher monoenoic acid and/or a derivative thereof, which is a higher monoenoic acid used in the present invention, is not particularly limited as long as it is pharmaceutically or sitologically permissible. That is, it is possible to use, directly or in suitable combination, natural fat having a large content of higher monoenoic acid, such as shark liver oil, whale oil, cod liver oil, rapeseed oil, mustered oil, cabbage seed oil, jojoba oil, and meadowfoam seed oil. Also, it is possible to extract and purify icosenic acid, docosenoic acid, and tetracosenoic acid from natural fat using ordinary methods, such as fractional distillation, crystallization, solvent extraction, urine clathration, and chromatography. More simply, it is possible to use a commercially available gondoic acid or erucic acid (products of Sigma Co.).

A so-called higher monoenoic acid derivative, which is a derivative of $C_{20}$ or higher monoenoic acid used in the present invention, includes derivatives of various esters and so forth besides salts of higher monoenoic acid. More specifically, examples of the higher monoenoic acid derivatives include salts of alkali metals, such as sodium and potassium, esters of lower aliphatic alcohols, such as ethanol, and mono-, di-, and tri-glycerides.

It is preferable that a fat composition for oral or enteral administration contain, per 1 gram of the fat composition, 20–200 mg of eicosapentaenoic acid and/or a derivative thereof, 20–200 mg of docosahexaenoic acid and/or a derivative thereof, and 100–400 mg of a $C_{20}$ or higher monoenoic acid and/or a derivative thereof. If the content of the fat composition is as described above, its hexacosanoic acid depressant function becomes conspicuous.

As a fat composition containing eicosapentaenoic acid and/or a derivative thereof, docosahexaenoic acid and/or a derivative thereof, and a $C_{20}$ or higher monoenoic acid and/or a derivative thereof, a cod liver oil (a product of Wakasa Co. for example, hereinafter referred to as prior art 2) used for the purpose of supplying Vitamins A and D is commercially available. However, as it is obvious from its purpose of supplying Vitamins A and D, the commercially available cod liver oil (for example, prior art 2) has a problem of having high content of Vitamins A and D. That is, in order to obtain a significant hexacosanoic acid depressant effect, it is necessary to intake more than a least effective dosage of the above-mentioned three kinds of fatty acids. However, if the commercially available cod liver oil (for instance, prior art 2) is used, Vitamins A and D are excessively taken as is partially described in the following Examples, and there is a large possibility that an excessive accumulation of Vitamins A and D is caused as described in the document Kenko•Eiyo Jyoho Kenkyuukai, "$6^{th}$ Edition Nihonjin no Eiyoushoyoryo shokujisessyu kijyun" Daiichi Shuppan, pp. 82–88, Sep. 10, 1999.

Accordingly, it is preferable that the fat composition for oral or enteral administration according the first embodiment of the present invention contain 75 µg or less and 2.5 µg or less of Vitamin A and Vitamin D, respectively, per 1 gram of the fat composition. In order to make the content of Vitamins A and D be 75 µg or less and 2.5 µg or less, respectively, each raw material of eicosapentaenoic acid and/or a derivative thereof, docosahexaenoic acid and/or a derivative thereof, and a $C_{20}$ or higher monoenoic acid and/or a derivative thereof which are purified as described above may be used. Also, it is possible to use a fat produced from the above-mentioned various natural fats by reducing the content of Vitamins A and D thereof. More specifically, it is possible to use cod liver oil in which the content of Vitamins A and D has been reduced by extraction and purification using fractional distillation or chromatography.

The fat composition for oral or enteral administration according to the first embodiment of the present invention may contain, other than the above-mentioned essential components, oil-soluble components, such as fats and fatty acids other than those mentioned above, within a range that does not harm the effect of the present invention. The fat composition for oral or enteral administration according to the first embodiment of the present invention may be prepared by mixing, agitating, and so forth the above-mentioned essential components and other arbitral components.

The effective dosage of the fat composition according to the first embodiment of the present invention for further improving the hexacosanoic acid depressant function when administered orally or enterally was determined to be 1–60 mg/body weight (kg)/day for eicosapentaenoic acid and/or a derivative thereof, 1–75 mg/body weight (kg)/day for docosahexaenoic acid and/or a derivative thereof, and 5–150 mg/body weight (kg)/day for a $C_{20}$ or higher monoenoic acid and/or a derivative thereof from experimental results of oral administration using mice.

Next, the second embodiment according to the present invention will be described.

The second embodiment according to the present invention is a hexacosanoic acid depressant including as active agents eicosapentaenoic acid and/or a derivative thereof, docosahexaenoic acid and/or a derivative thereof, and a $C_{20}$ or higher monoenoic acid and/or a derivative thereof, and it is possible to use the same eicosapentaenoic acid and/or a derivative thereof, docosahexaenoic acid and/or a derivative thereof, and a $C_{20}$ or higher monoenoic acid and/or a derivative thereof as described in the first embodiment.

It is preferable that a hexacosanoic acid depressant contain, as active ingredients, per 1 gram of the hexacosanoic acid depressant, the above-mentioned fatty acids, etc., including 20–200 mg of eicosapentaenoic acid and/or a derivative thereof, 20–200 mg of docosahexaenoic acid and/or a derivative thereof, and 100–400 mg of a $C_{20}$ or higher monoenoic acid and/or a derivative thereof. If the content of the hexacosanoic acid depressant is as described above, its hexacosanoic acid depressant function becomes conspicuous.

Also, for the same reasons as explained above, it is preferable that the hexacosanoic acid depressant contain 75 μg or less and 2.5 μg or less of Vitamin A and Vitamin D, respectively, per 1 gram of the hexacosanoic acid depressant. In order to make the content of Vitamins A and D be 75 μg or less and 2.5 μg or less, respectively, each raw material of eicosapentaenoic acid and/or a derivative thereof, docosahexaenoic acid and/or a derivative thereof, and a $C_{20}$ or higher monoenoic acid and/or a derivative thereof which are purified as described above may be used. Also, it is possible to use a fat which is prepared using the above-mentioned various natural fats by reducing the content of Vitamins A and D thereof.

The effective dosage of the hexacosanoic acid depressant according to the second embodiment of the present invention to further improve the hexacosanoic acid depressant function when administered orally or enterally was determined to be 1–60 mg/body weight (kg)/day for eicosapentaenoic acid and/or a derivative thereof, 1–75 mg/body weight (kg)/day for docosahexaenoic acid and/or a derivative thereof, and 5–150 mg/body weight (kg)/day for a $C_{20}$ or higher monoenoic acid and/or a derivative thereof from experimental results of oral administration using mice.

The hexacosanoic acid depressant according to the second embodiment of the present invention may be administered, for instance, orally, via tube, or enterally, to a human or an animal. Also, various forms may be selected for the hexacosanoic acid depressant among the general forms of pharmaceuticals based on the administration method and treatment purposes. Typical examples of such forms include, for instance, tablet, pill, powder, liquid, suspension, emulsion, granule, and capsule. The hexacosanoic acid depressant according to the second embodiment of the present invention may be prepared by mixing and agitating the above-mentioned essential components with an excipient, disintegrant, binder, coating, suspension agent, surfactant, stabilizer, isotonization agent, etc., which are generally used for the above forms of an agent.

Moreover, the hexacosanoic acid depressant according to the second embodiment of the present invention may be ingested as a nutritional composition in the form of a general food or drink as a means of diet therapy. The eicosapentaenoic acid and/or a derivative thereof, docosahexaenoic acid and/or a derivative thereof, and a $C_{20}$ or higher monoenoic acid and/or a derivative thereof, which are active agents of the present invention, were found to have very low toxicity, based on an acute toxicity tests using mice for oral administration, and its $LD_{50}$ was equal to or greater than 10 g/body weight (kg). Accordingly, the hexacosanoic acid depressant may be safely used to humans and animals with an extremely low probability of causing side effects.

Next, the present invention will be explained in detail using test examples.

Test 1:

This test was conducted in order to compare the present invention with conventional techniques using, as indices, a depression rate of hexacosanoic acid in erythrocyte membrane, and the concentration of vitamins A and D in blood.

(1) Preparation of Samples:

The following three kinds of samples were prepared.

Sample 1:

A capsule prepared in Example 1 of the present invention (which contains 80 mg/gram of eicosapentaenoic acid, 100 mg/gram of docosahexaenoic acid, and 180 mg/gram of a $C_{20}$ or higher monoenoic acid, and also contains 250 mg of a fat composition which contains substantially no Vitamins A and D).

Sample 2:

A capsule (which contains 250 mg of a fat composition corresponding to prior art 1) prepared in the same manner as in Example 1 except that 620 kg of soy bean oil (a product of Nisshin Oil Mills, Ltd.) was used instead of a purified fish oil having high content of eicosapentaenoic acid (a product of Nippon Suisan Kaisha, Ltd.), and a purified fish oil having high content of docosahexaenoic acid (a product of Croda Japan KK).

Sample 3:

A soft capsule which contains commercially available cod liver oil that is a fat composition corresponding to prior art 2 (a product of Wakasa Co. Ltd., which contains 80 mg/gram of eicosapentaenoic acid, 100 mg/gram of docosahexaenoic acid, and 180 mg/gram of a $C_{20}$ or higher monoenoic acid, and contains 1 gram of a fat composition containing 1200 μg and 9.5 μg, respectively, of Vitamins A and D).

(2) Testing Methods:

(a) Subjects and Administration Method:

Male volunteers (60 people with average body weight of 65 kg) collected from the company, whose hexacosanoic acid value in the erythrocyte membrane (i.e., the ratio of hexacosanoic acid to a total fatty acid) showed an abnormality (i.e., 0.20% or greater), were divided into three sample groups (i.e., 20 people in each group), and tests were conducted.

Also, each sample group was divided into four groups (i.e., a total of 12 groups) depending on the dosage of the fat composition (i.e., 1, 2, 5, and 7 gram/day), and the fat composition was administered to each person for eight weeks. No special diet was carried out.

(b) Method for Testing Depression Rate of Hexacosanoic Acid in Erythrocyte Membrane:

Prior to the administration of the samples, and after eight weeks since the start of the administration, 2 ml of whole blood samples were collected from each of the subjects using vacuum blood collecting tube (Terumo Corporation) including Na 2 EDTA. Each sample was centrifuged at 3,000 for 10 minutes, and an upper layer containing plasma was removed to use a lower layer including red blood cells as a sample to be analyzed. The values of hexacosanoic acid in erythrocyte membrane was analyzed by the BML INC., which is a large company commercially conducting laboratory tests (head office at T151-0051 5-21-3 Sendagaya, Shibuya-ku, Tokyo; http://www.bml.co.jp/). More specifically, lipids were extracted from the erythrocyte membrane using a solvent extraction method, and fatty acids, which are derivatives of the lipids, were obtained to quantify each fatty acid using a high performance liquid chromatography. In this manner, the ratio of the hexacosanoic acid to the total fatty acid was obtained (using the method described in Japanese Unexamined Patent Application, First publication, No. Hei 6-118078).

The depression rate (A) of the hexacosanoic acid was calculated using the following equation based on the value (B), which is a difference of the values of hexacosanoic acid of the samples between prior to and after eight weeks of the administration, and the value (C), which is the value of hexacosanoic acid prior to the administration of the samples:

$$A(\%)=(B/C)\times 100$$

(c) Method for Testing the Concentration of Vitamin A and Vitamin D (25-OH Vitamin D) in Blood:

After eight weeks of the administration of the samples, 2 ml of whole blood sample was collected from each of the subjects using vacuum blood collecting tube (Terumo Corporation) including a density gradient media. The sample was centrifuged at 3,000 for 10 minutes, and the upper layer of serum was used as a sample to be analyzed.

The samples were analyzed by the SRL, Inc., which commercially conducts laboratory tests (head office at T190-8567 2-41-19 Akebono-cho, Tachikawa-shi, Tokyo; http://www.srl-inc.co.jp/; refer to SRL 2000 Sogo Kensa Annai-shi for details of the analysis) using a high performance liquid chromatography for Vitamin A, and a competitive protein binding assay (CPBA) for 25-OH Vitamin D. Note that standard value (normal value) for Vitamin A, and 25-OH Vitamin D in blood is 20–83 µg/dl (65–276 IU/dl) and 10–55 ng/mg, respectively.

(3) Test Results:

Results of the tests are shown in Table 1. As obvious from Table 1, it is confirmed that the sample 1 of the present invention has a significant hexacosanoic acid depression rate as compared to the sample 3 (prior art 2), and in particular, to the sample 2 (prior art 1) which does not contain eicosapentaenoic acid and docosahexaenoic acid.

Also, it was confirmed that the concentration of Vitamins A and D in blood is maintained to be within the range of standard value (normal value) by the intake of the sample 1 of the present invention for a long period of time as compared with the sample 3 (prior art 2) having high contents of Vitamins A and D.

That is, in order to prevent the hypervitaminosis and to further improve the hexacosanoic acid depressant effect when orally or enterally adminisered, it is determined to be effective to prepare and use a fat composition which contains eicosapentaenoic acid and/or a derivative thereof, docosahexaenoic acid and/or a derivative thereof, and a $C_{20}$ or higher monoenoic acid and/or a derivative thereof, whose content of Vitamins A and D per 1 gram of the fat composition is 75 µg or less and 2.5 µg or less, respectively.

Note that when the tests were conducted by appropriately changing the kind of a $C_{20}$ or higher monoenoic acid, substantially the same results were obtained. Also, when the tests were conducted by appropriately changing the contents of Vitamins A and D within the range of 75 µg or less and 2.5 µg or less, respectively, per 1 gram of fat composition, substantially the same results were obtained.

TABLE 1

| Sample No. | Dosage (g/day) | Hexacosanoic acid depressant rate (%) | Vitamin A conc. in blood (µg/dl) | 25-OH Vitamin D conc. in blood (ng/ml) |
|---|---|---|---|---|
| 1 | 1 | 7 | 34 | 13 |
|   | 2 | 12 | 40 | 15 |
|   | 5 | 25 | 43 | 20 |
|   | 7 | 26 | 40 | 18 |
| 2 | 1 | 5 | 36 | 15 |
|   | 2 | 9 | 39 | 15 |
|   | 5 | 19 | 41 | 17 |
|   | 7 | 21 | 35 | 19 |
| 3 | 1 | 6 | 87 | 15 |
|   | 2 | 11 | 116 | 26 |
|   | 5 | 22 | 184 | 40 |
|   | 7 | 23 | 244 | 60 |

Test 2:

This test was conducted in order to determine a preferable amount of eicosapentaenoic acid and/or a derivative thereof, docosahexaenoic acid and/or a derivative thereof, and a $C_{20}$ or higher monoenoic acid and/or a derivative thereof in a fat composition having hexacosanoic acid depressant function.

(1) Preparation of Samples:

Samples of fat composition having the fatty acid contents shown in Table 2 were prepared. Note that the samples of the fat composition was prepared so that each sample had Vitamins A and D contents of 75 µg or less and 2.5 µg or less, respectively, per 1 gram of the fat composition.

TABLE 2

| | mg/g fat composition | | | |
|---|---|---|---|---|
| | Test Area 1 | Test Area 2 | Test Area 3 | Test Area 4 |
| $C_{20}$ or higher monoenoic acid | 70 | 100 | 400 | 500 |
| eicosapentaenoic acid | 10 | 20 | 200 | 230 |
| docosahexaenoic acid | 10 | 20 | 200 | 230 |

(a) Subjects and Administration Method:

Volunteers (40 people of 35 years old or older) collected from the company, whose hexacosanoic acid value in the erythrocyte membrane (i.e., the ratio of hexacosanoic acid to a total fatty acid) showed an abnormality (i.e., 0.20% or greater), were divided into four sample groups (i.e., 10 people in each group), and tests were conducted. Each of the samples was administered (5 grams/day) in the form of a gelatin capsule for eight weeks. No special diet was carried out.

(b) Method for Testing Depression Rate of Hexacosanoic Acid in Erythrocyte Membrane:

This test was conducted in the same manner as described in the above-mentioned Test 1.

(2) Test Results:

Results of the tests are shown in Table 3.

Note that although the hexacosanoic acid depressant rate of 26%, which was most effective, was obtained in the test area 4, decrease in the number of platelet was observed in six out of ten people. Accordingly, it was determined that it is preferable to have 20–200 mg of eicosapentaenoic acid, 20–200 mg of docosahexaenoic acid, and 100–400 mg of a $C_{20}$ or higher monoenoic acid per one gram of the fat composition in order to decrease hexacosanoic acid in the erythrocyte membrane.

Therefore, as a fat composition, which possesses hexacosanoic acid depressant function, for oral or enteral administration, a fat composition for oral or enteral administration having hexacosanoic acid depressant function that includes 20–200 mg of eicosapentaenoic acid, 20–200 mg of docosahexaenoic acid, and 100–400 mg of a $C_{20}$ or higher monoenoic acid per one gram of the fat composition, and further includes 75 µg or less and 2.5 µg or less of Vitamins A and D, respectively, per one gram of the fat composition is preferable.

Also, as a hexacosanoic acid depressant, a hexacosanoic acid depressant having hexacosanoic acid depressant function that includes as active ingredients 20–200 mg of eicosapentaenoic acid and/or a derivative thereof, 20–200 mg of docosahexaenoic acid and/or a derivative thereof, and 100–400 mg of a $C_{20}$ or higher monoenoic acid and/or a derivative thereof per one gram of the hexacosanoic acid depressant, and further includes 75 µg or less and 2.5 µg or less of Vitamins A and D, respectively, per one gram of the hexacosanoic acid depressant is preferable.

TABLE 3

| | Test Area 1 | Test Area 2 | Test Area 3 | Test Area 4 |
|---|---|---|---|---|
| hexacosanoic acid depressant rate (%) | 8 | 20 | 25 | 26 |

EMBODIMENTS

Next, the present invention will be explained in detail with reference to examples. However, the present invention is not limited to these examples by any means.

EXAMPLE 1

A fat composition having 80 mg of eicosapentaenoic acid, 100 mg of docosahexaenoic acid, and 180 mg of a $C_{20}$ or higher monoenoic acid, and which substantially contains no Vitamins A and D was prepared by mixing a commercially available purified rapeseed oil (380 kg; a product of Summit Seiyu Co. Inc.), purified fish oil having high content of eicosapentaenoic acid (260 kg; a product of Nisshin Oil Mills, Ltd.), purified fish oil having high content of docosahexaenoic acid (300 kg; a product of Croda Japan KK), and soybean oil (60 kg; a product of Nisshin Oil Mills, Ltd.).

Then, 250 mg of the fat composition was filled in a gelatin capsule No. 1 of Pharmacopeia of Japan (a product of Aliment Industry Co., Ltd.), and the contacting portion of the cap and the body of the capsule was sealed using a gelatin to produce three million capsules of hexacosanoic depressant.

When the capsules obtained were administered (20 capsules/day) to 10 volunteers from the company for eight weeks, whose hexacosanoic acid value in the erythrocyte membrane showed an abnormality (i.e., 0.20% or greater), the hexacosanoic acid value significantly improved.

EXAMPLE 2

A fat composition which includes eicosapentaenoic acid, docosahexaenoic acid, and a $C_{20}$ or higher monoenoic acid, and which substantially contains no Vitamins A and D, was prepared by mixing a commercially available gadoleic acid (1 kg; a product of Sigma Co.), erucic acid (560 g; a product of Sigma, Co.), menhaden oil (containing 11% eicosapentaenoic acid and 14% docosahexaenoic acid; 2760 g; a product of Sigma Co.), and absolute ethanol (3 kg; a product of Wako Pure Chemical Industries, Ltd.) to be a uniform solvent.

Then, calcium carbonate (5680 g, a product of Wako Pure Chemical Industries, Ltd.) was added to a mixed solution of the fat composition obtained, and the mixture was kneaded to be uniform. After this, the mixture was dried at 40° C. to remove ethanol.

The composition obtained was formed into a tablet using a tabletting machine (a product of Hatake Tekkosho) by directly hitting the composition with a pressure of 3 t/m², and tablets of 10 mm diameter having a weight of 400 mg were obtained.

The surface of each tablet was covered by spraying a uniform solution formed by mixing 8.5 kg of hydroxylpropylmethylcellulose phthalate (a product of Shin-Etsu Chemical Co., Ltd.) with 100 kg of acetone (a product of Mitsui Petrochemical Industries, Ltd.) to produce 20,000 hexacosanoic acid depressant tablets (weight of 440 mg, containing 12 mg of eicosapentaenoic acid, 15 mg of docosahexaenoic acid, and 62 mg of a $C_{20}$ or higher monoenoic acid per tablet, which substantially contained no Vitamins A and D).

When the tablets obtained were administered (30 capsules/day) to 10 volunteers from the company for eight weeks, whose hexacosanoic acid value in the erythrocyte membrane showed an abnormality (i.e., 0.20% or greater), the hexacosanoic acid value significantly improved.

EXAMPLE 3

A fat composition which includes, per one gram of the composition, 70 mg of eicosapentaenoic acid, 60 mg of docosahexaenoic acid, and 110 mg of a $C_{20}$ or higher monoenoic acid, and which substantially contained no Vitamins A and D, was prepared by mixing a commercially available gondoic acid (600 g; a product of Sigma Co.), erucic acid (500 g; a product of Sigma, Co.), docosahexaenoic acid (600 g; a product of Sigma Co.), and purified olive oil (7.6 kg; a product of Nacalai tesque).

Then, 300 mg of the fat composition was filled in a gelatin capsule No. 1 of Pharmacopeia of Japan (a product of Aliment Industry Co., Ltd.), and the contacting portion of the cap and the body of the capsule was sealed using a gelatin to produce three million capsules of hexacosanoic depressants.

When the capsules obtained were administered (40 capsules/day) to 10 volunteers from the company for eight weeks, whose hexacosanoic acid value in the erythrocyte membrane showed an abnormality (i.e., 0.20% or greater), the hexacosanoic acid value is significantly improved.

INDUSTRIAL APPLICABILITY

The fat composition for oral or enteral administration and a hexacosanoic acid depressant according to the present invention have a hexacosanoic acid depression function and can improve an aging inhibitory effect on cell membranes. Accordingly, they may be effectively used for the prevention and treatment of lifestyle-related diseases.

What is claimed is:

1. A fat composition for oral administration which comprises 20 to 200 mg of eicosapentaenoic acid and/or a derivative thereof per one gram of the fat composition, 20 to 200 mg of docosahexaenoic acid and/or a derivative thereof per one gram of the fat composition, 100 to 400 mg of a $C_{20}$ or higher monoenoic acid and/or a derivative thereof per one gram of the fat composition, and reduces hexacosanoic acid at a rate of at least 20% in erythrocyte membrane.

2. A fat composition for oral administration according to claim 1, which further comprises Vitamins A and D and wherein the content of Vitamins A and D per one gram of the fat composition is 75 μg or less and 2.5 μg or less, respectively.

3. A hexacosanoic acid depressant composition which comprises as active ingredients 20 to 200 mg of eicosapentaenoic acid and/or a derivative thereof per one gram of the composition 20 to 200 mg of docosahexaenoic acid and/or a derivative thereof per one gram of the composition, 100 mg to 400 mg of a $C_{20}$ or higher monoenoic acid and/or a derivative thereof per one gram of the composition and optionally Vitamins A and D, wherein the hexacosanoic acid depressant composition reduces hexacosanoic acid at a rate of at least 20% in erythrocyte membrane.

4. A hexacosanoic acid depressant composition according to claim 3, wherein the content of Vitamins A and D per one gram of the hexacosanoic acid depressant is 75 μg or less and 2.5 μg or less, respectively.

5. A method of reducing hexacosanoic acid in a subject, measured as a ratio of hexacosanoic acid to total fatty acid, said method comprising orally administering eicosapentaenoic acid and/or a derivative thereof in an amount of 1 to 60 mg/body weight (kg)/day docosahexaenoic acid and/or a derivative thereof in an amount of 1 to 75 mg/body weight (kg)/day, and a $C_{20}$ or higher monoenoic acid and/or a derivative thereof in an amount of 5 to 150 mg/body weight (kg)/day, provided that hexacoanoic acid is reduced at least 20% in erythrocyte membrane.

* * * * *